US00PP22716P2

(12) United States Plant Patent
Malone et al.

(10) Patent No.: US PP22,716 P2
(45) Date of Patent: May 8, 2012

(54) APRICOT TREE NAMED 'CLUTHA SUMMER'

(50) Latin Name: *Prunus armeniaca*
Varietal Denomination: Clutha Summer

(75) Inventors: Michael T. Malone, Havelock North (NZ); Arlene E. Nixon, Central Otago (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 0 days.

(21) Appl. No.: 13/136,018

(22) Filed: Jul. 19, 2011

(51) Int. Cl.
*A01H 5/00* (2006.01)

(52) U.S. Cl. ..... Plt./186

(58) Field of Classification Search ..... Plt./186
See application file for complete search history.

*Primary Examiner* — Howard Locker
(74) *Attorney, Agent, or Firm* — Greenlee Sullivan P.C.

(57) ABSTRACT

A new and distinct apricot variety is described. The variety results from the open pollination of the variety 'Goldstrike' (U.S. Plant Pat. No. 7,035). Seedlings generated from the open pollination were planted at Clyde, Otago, New Zealand. In 2002 D14/1 was identified as having potential as a new variety, it has since been given the denomination 'Clutha Summer'. The fruit of 'Clutha Summer' have been shown to have a very attractive appearance with between 25 to 85% cover of a deep rose red blush, along with a superb flavour. This variety is also characterised by its firm melting, semi-cling stone flesh, excellent keeping quality, and the timing of harvest.

4 Drawing Sheets

Genus and species of plant claimed: *Prunus armeniaca.*
Variety denomination: 'CLUTHA SUMMER'.

BACKGROUND OF THE INVENTION

Seedlings obtained from the deliberate open pollination of 'Goldstrike' (U.S. Plant Pat. No. 7,035) at Clyde, Otago, New Zealand, were planted out in 1998. In January 2002 D14/1 was identified as having potential as a new variety, later in 2002 D14/1 was first asexually propagated by budding onto 'Golden Queen' (not patented) seedlings and trees were planted out in Clyde during the southern hemisphere winter of 2003. The resulting plants propagated true to type, demonstrating that the characteristics of the new variety are stable and transmitted without change through succeeding generations. D14/1 has since been named 'Clutha Summer'.

SUMMARY OF THE INVENTION

'Clutha Summer' is a new and distinct apricot variety. Under the New Zealand growing conditions 'Clutha Summer' is distinguished from its known parent 'Goldstrike' and a number of other varieties such as 'Sundrop' (not patented) and 'Alex' (U.S. Plant Pat. No. 11,721) by the following characteristics:

'Goldstrike' is a vigorous tree with an upright, then spreading habit while 'Clutha Summer' has a medium vigour with an open spreading habit. The fruit of 'Goldstrike' is free stone with a reddish-purple blush whereas the fruit of 'Clutha Summer' is semi-cling stone with a deep red blush.

The fruit of 'Clutha Summer' is larger with a better eating quality and longer storage life than that of 'Sundrop'.

The fruit of 'Clutha Summer' is larger than that of 'Alex' and the flowers are self fertile while 'Alex' requires a pollinizer. Fruit of 'Clutha Summer' also matures 2 weeks before that of 'Alex'.

DETAILED DESCRIPTION

Figure 1:
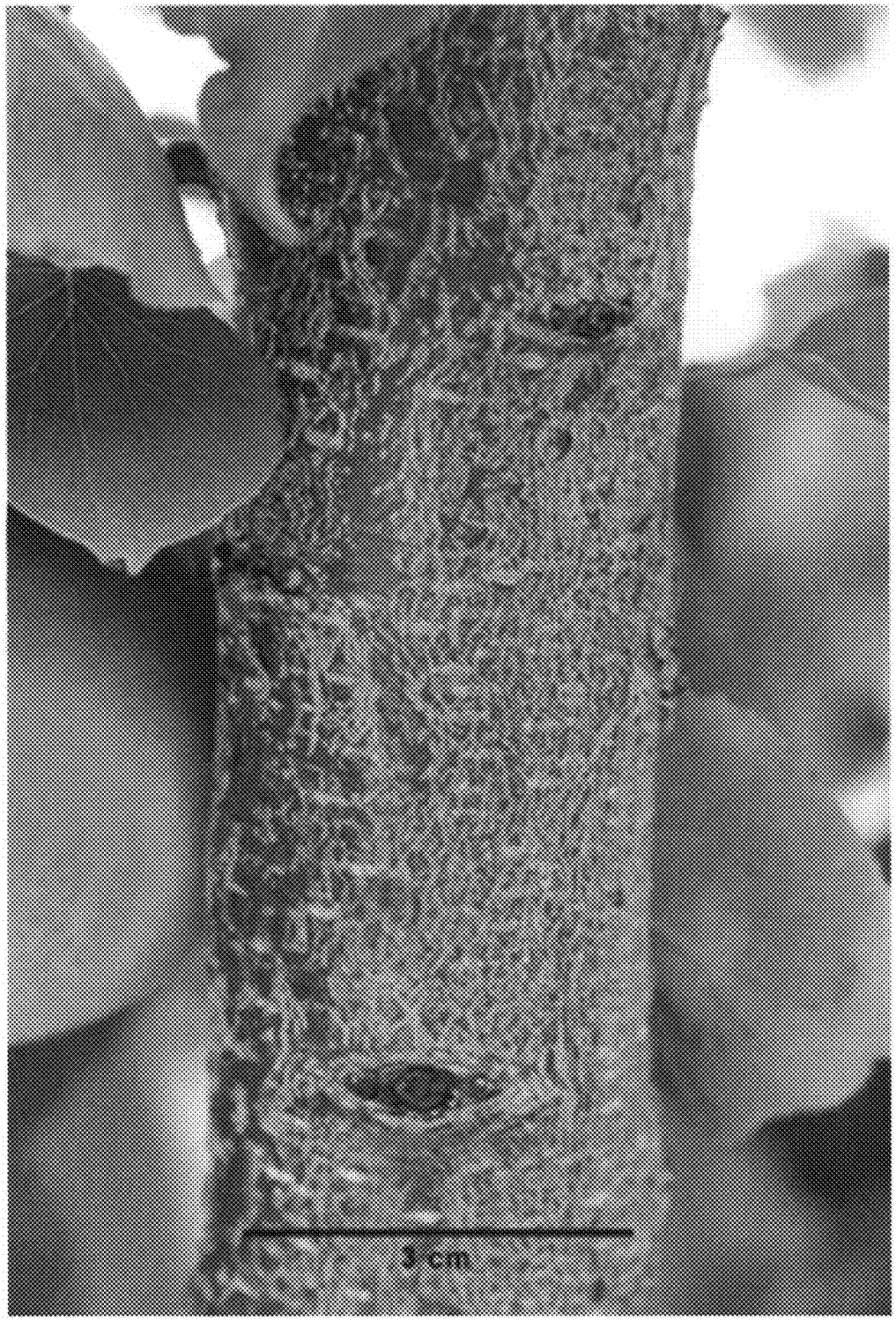
FIG. 1: 'Clutha Summer' branch, showing branch colour, bark texture and lenticels.
Figure 2:
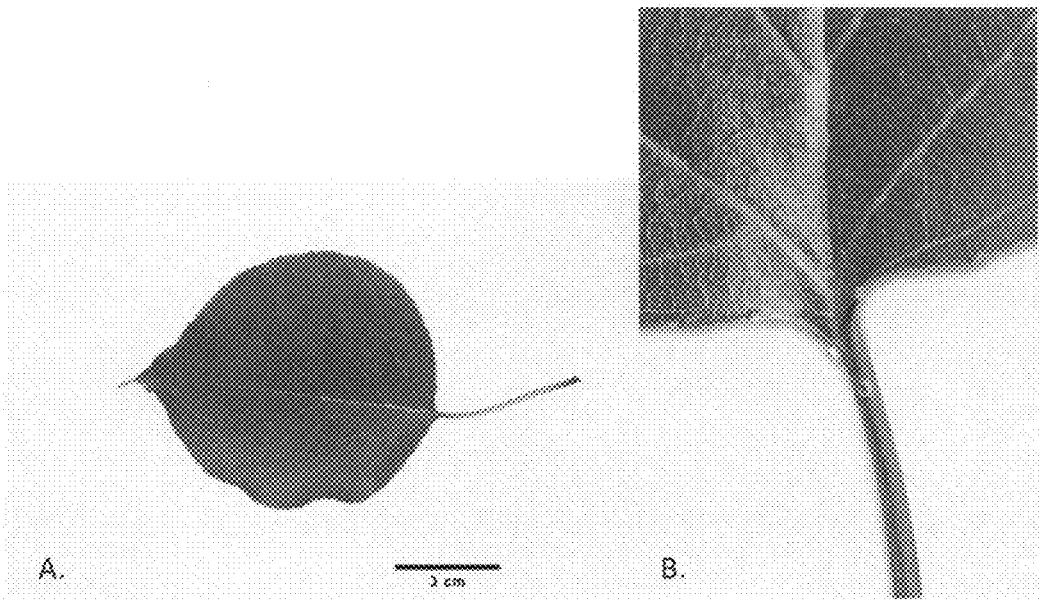
FIG. 2: A fully expanded leaf of 'Clutha Summer' (A) and a close up of the petiole showing the petiole glands (B).
Figure 3:
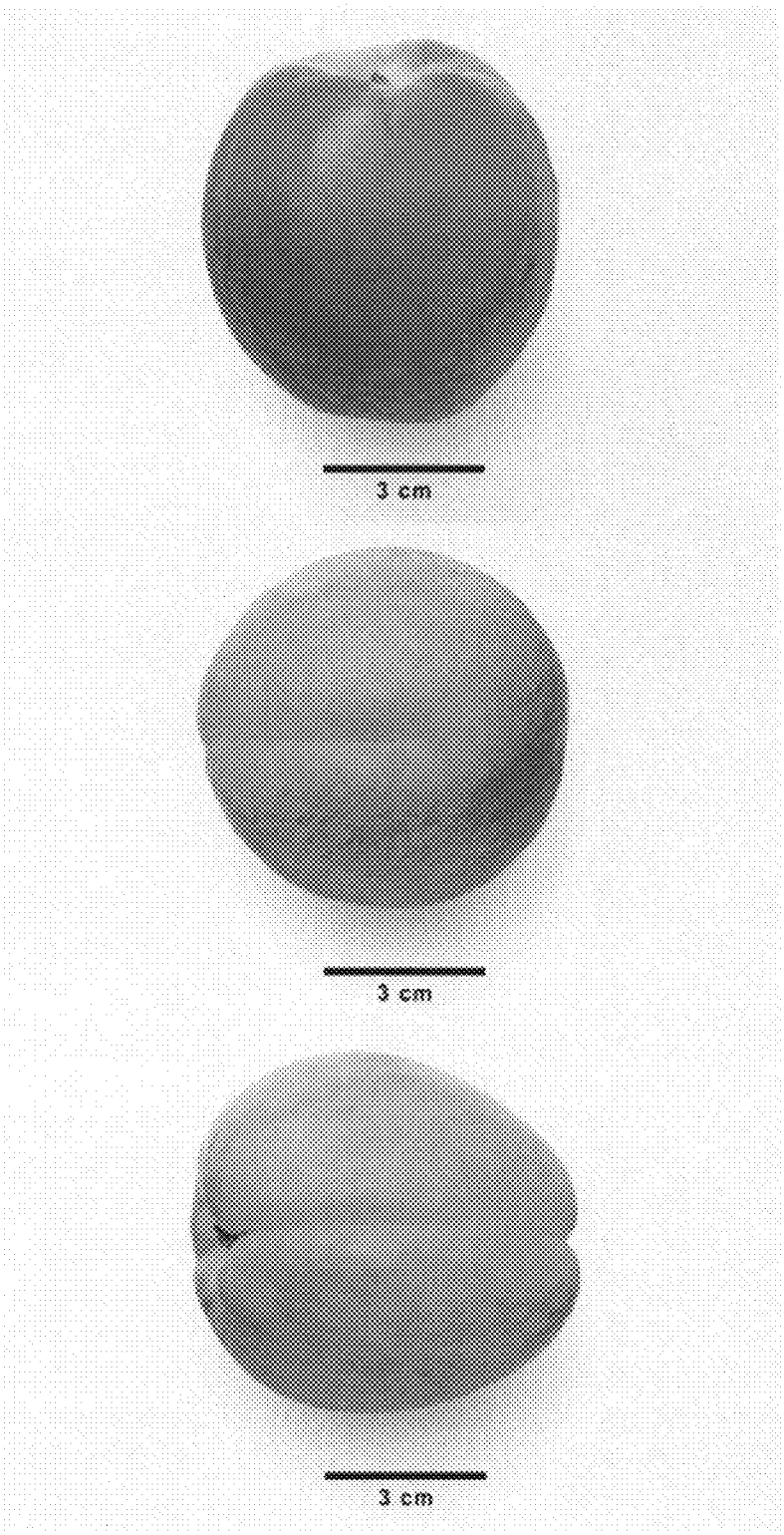
FIG. 3: Three views of whole 'Clutha Summer' fruit.
Figure 4:
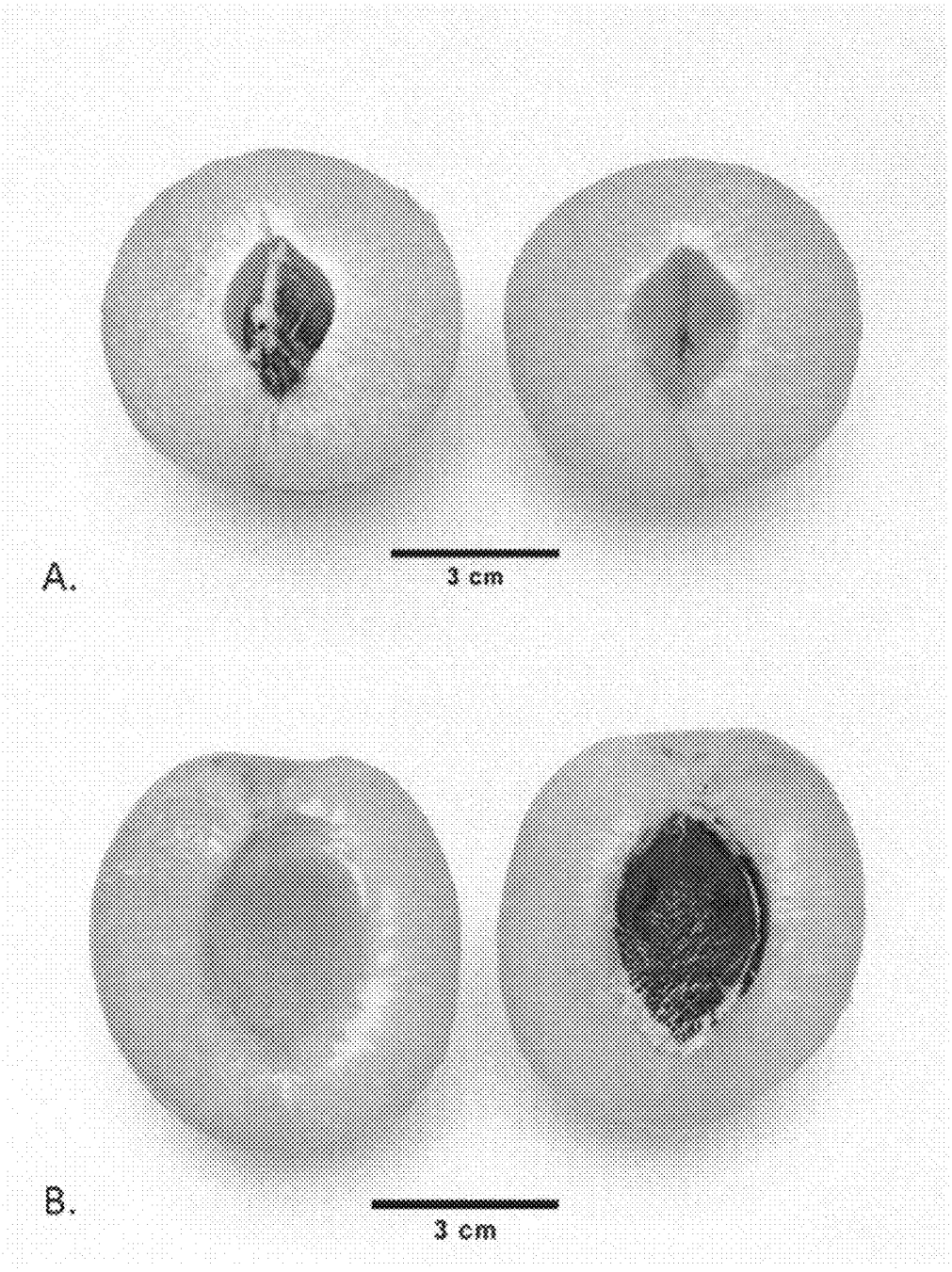
FIG. 4: Transverse (A) and longitudinal (B) sections of 'Clutha Summer' fruit.

The following is a brief description of the new variety with colour terminology in accordance with The Royal Horticultural Society Colour Charts (R.H.S.C.C.) 2001 edition. The specimens described were grown at Clyde, New Zealand. The observations were made over the 2009-2011 seasons on mature trees which were planted in 2005.

Tree: Average of approximately 3-4 m tall at maturity with a spread of approximately 2.5-3 m, medium vigour with an upright to spreading habit when pruned to a typical 3-4 leader vase shape. 'Clutha Summer' scions are compatible on both peach seedlings ('Golden Queen') and 'Myrobalan B' (plum) (not patented) root stocks. Tree health is considered to be good under South Otago conditions in New Zealand with high productivity, up to an average of approximately 2.5 kg/mature tree, and a similar precocity to commercially grown varieties in the area.

Trunk: Average circumference of a mature trunk, approximately 30 cm from the ground is 37 cm. Trunk colour was observed to be near greyed brown 200B. The branch colour was observed to be near greyed orange 177A.

Leaves: The leaves examined were fully expanded and harvested from physiologically mature trees. The overall shape of the leaves was ovate with a broad long acuminate tip, an attenuate to obtusely cunate base and crenulate margins. Leaves are arranged alternatively. The colour of the upper side of the leaf was near green group 137A and moderately glossy, while the lower side was near green 137C.

Petiole: The average petiole length of fully expanded leaves was 40 mm. The colour of the upper side of the petiole was observed to be near greyed purple 183 A, and near greyed purple 183 D on the lower side. Petioles were observed to have, on average, two glands at the leaf end.

Buds: 2 mm wide, 3 mm long and near grey purple 187 A in colour.

Flowers: Flower observations were made at full bloom. Bud burst was been recorded in early September (approximately 5th September), with full bloom occurring mid September (approximately 12th September), and petal fall occurring late September. The average diameter of an open flower was 30.8 mm. Flower bud density is high. Flowers have a subtle fragrance. Flowers are borne on spurs with an average of 3 to 5 flowers per spur.

Corolla: Five petals per flower, with an average length of 16 mm and average width of 15 mm. Petals are arranged in a slightly overlapping pattern. The majority of the petals observed had a smooth margin with the occasional one displaying slight crenulation at the tip. Petals are white at full bloom with pale pink veins.

Stamens: An average of 29 per flower. Filaments were an average length of 8.5 mm and translucent white in colour. Anthers were coloured near yellow orange 17 C, with pollen coloured near greyed yellow 163 B.

Carpel: Pistil length is on average approximately 18.5 mm.

Pedicel: Average length 2.5 mm and pale green in colour.

Calyx: Five sepals per flower, average length of 6.5 mm and width 5 mm with an acute apex and smooth margin. Colour near red purple 59 B.

Buds: 2.5 mm wide, 4.5 mm long and ovoid in shape. Colouration was near greyed purple N186C. Observations were taken at the winter bud stage.

Fruit size: Fruit at horticultural maturity were on average between 120 and 150 g. Average height of 63.5 mm, width (lateral) 57.93 mm, and width (ventral) 58.22 mm.

Fruit shape: Fruit are symmetric, and ovate in shape, with a slightly sunken suture.

Fruit skin: Fruit surface is smooth with minimal pubescence. Background colouration is near orange 26B.

Fruit over colour: Covers between 25-85% of the fruit surface in a solid flush with a colour near red 46A.

Fruit flesh: Fine grained and consistently dense, with a medium firmness and melting texture. Fruit firmness was measured at 2.5 kgf at the first harvest on 9th January, and 2.7 kgf at the second harvest on 12th January. Colour is near orange 26 B with no whiteness around the stone, the stone cavity colour is near orange 26 A.

Fruit stone: Elliptic in shape with a retuse apex and no mucro. Average weight was 4.7 g, with an average height of 32 mm, width (lateral) 22 mm, and width (ventral) 11 mm. Stone is semi-cling and has a colour near greyed orange 165 B.

Fruit flavour: Sweet distinct apricot flavour. Soluble solids percentage has been recorded at an average of 15.1 with a pH of 4.6 in fruit from the first harvest on 9th January and 14.1 and 4.4 respectively at the second harvest at 12th January.

Use: Fresh eating.

Keeping quality: Has been shown to store very well for at least four weeks.

We claim:

1. A new and distinct apricot plant substantially as illustrated and described.

* * * * *